United States Patent

Fikentscher et al.

Patent Number: 5,155,270
Date of Patent: Oct. 13, 1992

[54] ANIONICALLY POLYMERIZED N-VINYLFORMAMIDE AND THE PREPARATION THEREOF

[75] Inventors: Rolf Fikentscher, Ludwigshafen; Michael Kroener, Mannheim, both of Fed. Rep. of Germany

[73] Assignee: BASF Aktiengesellschaft, Ludwigshafen, Fed. Rep. of Germany

[21] Appl. No.: 754,664

[22] Filed: Sep. 4, 1991

[30] Foreign Application Priority Data

Sep. 26, 1990 [DE] Fed. Rep. of Germany ....... 4030380

[51] Int. Cl.$^5$ ........................................... C07C 233/03
[52] U.S. Cl. .................................................. 564/159
[58] Field of Search ..................... 564/159, 152, 215

[56] References Cited

U.S. PATENT DOCUMENTS 3,424,791 1/1969 Kurtz et al. .
4,421,602 12/1983 Brunnmueller et al. .......... 162/168.2
4,444,667 4/1984 Burkert et al. ...................... 210/735

FOREIGN PATENT DOCUMENTS 184074 6/1986 European Pat. Off. .
1094794 12/1967 United Kingdom .

Primary Examiner—Joseph L. Schofer
Assistant Examiner—M. Nagumo
Attorney, Agent, or Firm—Oblon, Spivak, McClelland, Maier & Neustadt

[57] ABSTRACT

Poly-N-vinylformamide which contains structural units of the formula

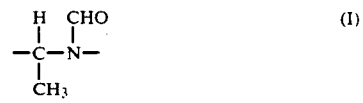

and a terminal double bond of the formula

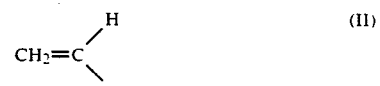

is prepared by anionic polymerization of N-vinylformamide in the presence of bases.

2 Claims, No Drawings

ANIONICALLY POLYMERIZED N-VINYLFORMAMIDE AND THE PREPARATION THEREOF

The present invention relates to poly-N-vinylformamides which can be obtained by anionic polymerization, and to a process for the preparation thereof.

The polymerization of N-vinylformamide has to date been carried out with initiators which decompose under the polymerization conditions into radicals, such as peroxides or azo compounds. A process of this type is described, for example, in EP-C 71 050. The free-radical polymerization of N-vinylformamide leads to C-C linkage of the monomers, resulting in linear polymers which contain repeating units of the formula

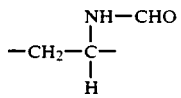

The preparation of N-vinylformamide is disclosed, for example, in DE-C 1 224 304 and EP-C 184 074.

It is an object of the invention to provide novel polymers based on N-vinylformamide and a process for the preparation thereof.

We have found that this object is achieved by anionically polymerized N-vinylformamide, which contains structural units of the formula

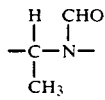

and a terminal double bond of the formula

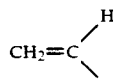

In contrast to the polymerization initiated by free radicals, the base-catalyzed polymerization of N-vinylformamide, ie. the compound of the formula

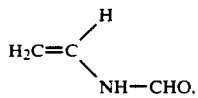

results in C-N linkage of at least 2 monomer molecules so that the resulting polymers contain structural units of the abovementioned formula I.

The N-vinylformamide polymerization according to the invention takes place in the presence of bases. Examples of suitable bases are metal alcoholates, eg. sodium methylate, potassium t-butylate, sodium and potassium isopropylate, metal hydrides, eg. $NaBH_4$, metal alkyls such as butyllithium, metal amides such as sodamide and lithium diisopropylamide, alkali metal and alkaline earth metal cyanides such as sodium cyanide and potassium cyanide, tertiary bases such as trimethylamine, triethylamine, tripropylamine, pyridine, triethanolamine, and sodium hydroxide, potassium hydroxide, lithium hydroxide, magnesium hydroxide, magnesium oxide, calcium oxide, calcium hydroxide and barium oxide. The anionic polymerization of N-vinylformamide can be carried out in bulk or in organic solvents. Examples of suitable organic solvents are aprotic polar compounds such as acetonitrile, glycol ethers, dioxane or mixtures thereof, or nonpolar solvents are used, such as $C_5$-$C_{20}$-hydrocarbons, for example pentane, hexane, cyclohexane, octane or petroleum fractions. When nonpolar solvents are used, the polymerization is an emulsion polymerization. The anionic polymerization can be carried out in a wide temperature range, eg. from $-80°$ to $+150°$ C., preferably from $10°$ to $80°$ C. The temperature essentially depends on the base used as catalyst and on the amount thereof. In general, from 0.1 to 20, preferably 1 to 10, mol %, based on N-vinylformamide, of base is used.

Of particular industrial interest is the bulk polymerization of N-vinylformamide using tertiary bases such as, in particular, trimethylamine. Under relatively mild reaction conditions, eg. at from $20°$ to $30°$ C., dimeric N-vinylformamide of the formula

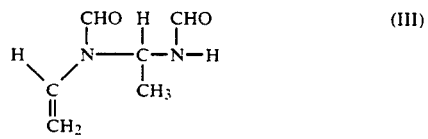

is obtained in from a few hours to several days.

The anionic polymerization of N-vinylformamide using, for example, trimethylamine stops at the stage of the dimer of the formula III under the conditions described above. Under forcing conditions or with the addition of another base, eg. sodium methylate, III undergoes anionic polymerization with further N-vinylformamide to give higher molecular weight products which have K values of from 1 to 50.

Dimeric N-vinylformamide of the formula III is an interesting intermediate. Further polymerization of it is possible not only by an anionic but also by a free-radical mechanism, with the formation of high molecular weight polymers. Particularly high molecular weight polymers are obtained, for example, by water-in-oil polymerization or inverse suspension polymerization of III with azo initiators, conventional peroxides or sodium, potassium or ammonium persulfate. The compound of the formula III can be thermally cleaved to N-vinylformamide. Since the compound is stable on storage, it is obvious to convert N-vinylformamide, which gives rise to problems on storage, into the dimer and to store and transport it in this form. N-vinylformamide can be recovered therefrom as required by thermal cleavage as described above.

After the polymerization is complete, the bases used as catalyst are removed from the reaction mixture. This is particularly straightforward when relatively volatile bases such as trimethylamine are used as catalyst, because these bases can be distilled out of the polymer under reduced pressure, eg. under from 5 to 50 mbar, at from $10°$ to $30°$ C. If anion exchangers have been used as catalyst for the polymerization of N-vinylformamide, they can be removed, for example, by filtration or centrifugation.

Polymers which contain structural units of the formula I and a terminal double bond of the formula II can be further modified and employed, for example, in the paper industry.

The K values were determined by the method of H. Fikentscher, Cellulose Chemie 13 (1932) 58-64 and 71-74, where $K = k \times 10^3$. The measurements were carried out on 1% strength aqueous solutions of the polymers at 25° C. and pH 7. The % data are percent by weight.

EXAMPLE 1

21.3 g of N-vinylformamide are placed in a polymerization apparatus, 1.7 g of potassium t-butylate are added and the mixture is stirred under a nitrogen atmosphere at 30° C. for 16 hours. 98% of the N-vinylformamide has reacted after this time. A viscous composition is obtained and is dissolved in 15 g of methanol and neutralized by addition of methanolic hydrochloric acid. The precipitated potassium chloride is filtered off, and the filtrate is evaporated under reduced pressure at up to 80° C. The residue comprises 20 g of an anionically polymerized N-vinylformamide with a K value of 6.

EXAMPLE 2

3550 g of N-vinylformamide are introduced into a polymerization apparatus and stirred under a nitrogen atmosphere. At 25° C., 195 g of trimethylamine are introduced over the course of 60 minutes. The reaction mixture is stirred at room temperature, with cooling, for a total of 42 hours. The conversion is 95% after this time. The reaction mixture contains 3322 g of dimeric N-vinylformamide of the formula III. Working up in several stages by distillation in a thin film evaporator results in a 99% pure dimer of molecular weight 142. The iodine number, elemental analysis and $^1$H NMR spectrum are entirely consistent with the structure. The boiling point of dimeric N-vinylformamide is 127° C. under 0.2 mbar.

EXAMPLE 3

35.5 g of N-vinylformamide are introduced into a polymerization apparatus, 0.6 g of LiOH is added and the mixture is stirred at 25° C. under a nitrogen atmosphere for 10 hours. 94% of the N-vinylformamide has reacted after this time. The reaction mixture contains 27.0 g of dimeric N-vinylformamide in addition to 6.4 g of oligomers.

EXAMPLE 4

35.5 g of N-vinylformamide are introduced into a polymerization apparatus, 4.9 g of potassium acetate are added and the mixture is stirred at 50° C. for 23 hours and at 60° C. for 6 hours under a nitrogen atmosphere at 30° C. 92% of the N-vinylformamide has reacted after this time. The reaction mixture contains 29.5 g of dimeric N-vinylformamide in addition to 3.1 g of oligomers.

EXAMPLE 5

71 g of N-vinylformamide and 71 g of acetonitrile are introduced into a polymerization apparatus, 4.1 g of sodium methylate are added and the mixture is stirred at 25° C. for 5.5 hours. The mixture is then cooled to 0° C. and 35.1 g of 5.5% by weight methanolic HCl solution are added. The precipitated NaCl is filtered off, and the mother liquor is concentrated under reduced pressure at not above 30° C. GPC analysis of the 70 g of residue gives the following result:

| | |
|---|---|
| N-Vinylformamide: | 12.5% |
| Dimer: | 75.1% |
| Trimer: | 11.9% |
| Tetramer: | 0.5% |

We claim:
1. Anionically dimerized N-vinylformide, which has the formula

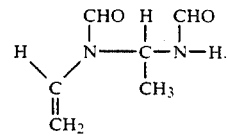

2. A process for preparing dimeric N-vinylformamide as claimed in claim 1, which comprises exposing N-vinylformamide to tertiary amines at from 10° to 50° C.

* * * * *